US009067000B2

(12) United States Patent
DesNoyer et al.

(10) Patent No.: US 9,067,000 B2
(45) Date of Patent: *Jun. 30, 2015

(54) END-CAPPED POLY(ESTER AMIDE) COPOLYMERS

(71) Applicant: ABBOTT CARDIOVASCULAR SYSTEMS INC., Santa Clara, CA (US)

(72) Inventors: Jessica Renee DesNoyer, Bedford, MA (US); Stephen Dirk Pacetti, San Jose, CA (US); Vidya Nayak, Cupertino, CA (US); Lothar Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/083,226

(22) Filed: Nov. 18, 2013

(65) Prior Publication Data

US 2014/0107148 A1  Apr. 17, 2014

Related U.S. Application Data

(63) Continuation of application No. 12/409,129, filed on Mar. 23, 2009, now Pat. No. 8,603,634, which is a continuation-in-part of application No. 10/975,247, filed on Oct. 27, 2004, now abandoned.

(51) Int. Cl.
| | |
|---|---|
| *A61K 31/765* | (2006.01) |
| *A61K 33/00* | (2006.01) |
| *A61F 2/06* | (2013.01) |
| *C08L 77/12* | (2006.01) |
| *A61L 31/06* | (2006.01) |
| *A61L 27/34* | (2006.01) |
| *A61L 31/10* | (2006.01) |

(52) U.S. Cl.
CPC ............... *A61L 31/06* (2013.01); *A61L 27/34* (2013.01); *A61L 31/10* (2013.01)

(58) Field of Classification Search
USPC ............... 424/78, 37, 422, 423, 426, 486; 428/423.1, 474.4; 525/420, 434; 528/288, 302, 307, 308, 323, 324, 325; 528/326, 329.1, 330, 331, 332, 335; 604/48, 500, 890.1; 623/1.1
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |

(Continued)

FOREIGN PATENT DOCUMENTS

| | | |
|---|---|---|
| DE | 42 24 401 | 1/1994 |
| EP | 0 514 406 | 11/1992 |

(Continued)

OTHER PUBLICATIONS

U.S. Appl. No. 10/816,072, filed Mar. 31, 2004, Dugan et al.
Anonymous, *Cardiologists Draw-Up The Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

(Continued)

*Primary Examiner* — Ana Woodward
(74) *Attorney, Agent, or Firm* — Squire Patton Boggs (US) LLP

(57) ABSTRACT

This invention relates to poly(ester amide)s (PEAs) comprising inactivated terminal amino and carboxyl groups, methods of synthesizing the inactivated PEAs and uses for them in the treatment of vascular diseases.

3 Claims, No Drawings

(56) References Cited

U.S. PATENT DOCUMENTS

| | | |
|---|---|---|
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,365,172 B1 | 4/2002 | Barrows |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |

(56) References Cited

U.S. PATENT DOCUMENTS

| | | |
|---|---|---|
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,703,040 B2 | 3/2004 | Katsarava et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,830,747 B2 | 12/2004 | Lang et al. |
| 6,926,919 B1 | 8/2005 | Hossainy et al. |
| 7,056,591 B1 | 6/2006 | Pacetti et al. |
| 7,063,884 B2 | 6/2006 | Hossainy et al. |
| 7,166,680 B2 | 1/2007 | Desnoyer et al. |
| 7,220,816 B2 | 5/2007 | Pacetti et al. |
| 7,390,497 B2 | 6/2008 | DesNoyer et al. |
| 7,435,788 B2 | 10/2008 | Pacetti et al. |
| 7,820,732 B2 | 10/2010 | Tang et al. |
| 7,879,356 B2 | 2/2011 | Cohn et al. |
| 8,192,752 B2 | 6/2012 | Tang et al. |
| 2001/0007083 A1 | 7/2001 | Roorda |
| 2001/0009662 A1 | 7/2001 | Cohn et al. |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0027940 A1 | 2/2003 | Lang et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0106204 A1 | 5/2005 | Hossainy et al. |
| 2005/0208091 A1 | 9/2005 | Pacetti |
| 2005/0265960 A1 | 12/2005 | Pacetti et al. |
| 2005/0271700 A1 | 12/2005 | Desnoyer et al. |

FOREIGN PATENT DOCUMENTS

| | | |
|---|---|---|
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | EP 0 301 856 | 2/1989 |
| SU | EP 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |

(56) References Cited

FOREIGN PATENT DOCUMENTS

| | | |
|---|---|---|
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Chung et al., *Inner core segment design for drug delivery control of thermo-responsive polymeric micelles*, Journal of Controlled Release 65:93-103 (2000).
De Lezo et al., *Intracoronary Ultrasound Assessment of Directional Coronary Atherectomy: Immediate and Follow-Up Findings*, JACC vol. 21, No. 2, (1993) pp. 298-307.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials For Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Moreno et al., *Macrophage Infiltration Predicts Restenosis After Coronary Intervention in Patients with Unstable Angina*, Circulation, vol. 94, No. 12, (1996) pp. 3098-3102.
Nordrehaug et al., *A novel biocompatible coating applied to coronary stents*, EPO Heart Journal 14, p. 321 (p. 1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin III upon inactivation of thrombin and coagulaton Factor Xa*, Biochem J. 262, (1989) pp. 651-658.
Search Report for PCT/US2005/037326, filed Oct. 18, 2005, mailed Apr. 6, 2006, 14 pgs.
Shigeno, *Prevention of Cerebrovascular Spasm By Bosentan, Novel Endothelin Receptor*; Chemical Abstract 125:212307 (1996).
van Beusekom et al., *Coronary stent coatings*, Coronary Artery Disease 5(7):590-596 (Jul. 1994).
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).

END-CAPPED POLY(ESTER AMIDE) COPOLYMERS

FIELD

This invention generally relates to end-capped poly(ester amide) copolymers useful in the manufacture or coating of an implantable medical device.

BACKGROUND

Poly(ester amide)s (PEAs) are useful as polymeric carriers of bioactive substances when coated on implantable medical devices such as stents to reduce restenosis and other problems associated with the treatment of atherosclerosis (see, e.g., U.S. Pat. No. 6,503,538, B1).

PEAs can be made by condensation polymerization of a diamino compound with a diester dicarboxylic acid (Scheme I). In Scheme I, the dicarboxylic acids are converted to an active di-p-nitrophenyl derivative to facilitate the polymerization.

When the dicarboxylic acid and the diamino subunits are used stoichiometrically, the PEA formed has one terminal carboxylic acid group and one terminal amino group. When the dicarboxylic acid and the diamino subunits are not used in a 1:1 ratio, the PEA formed can have excess terminal carboxylic acid groups if more of the dicarboxylic acid subunit is used or excess terminal amino groups if more of the diamino subunit is used.

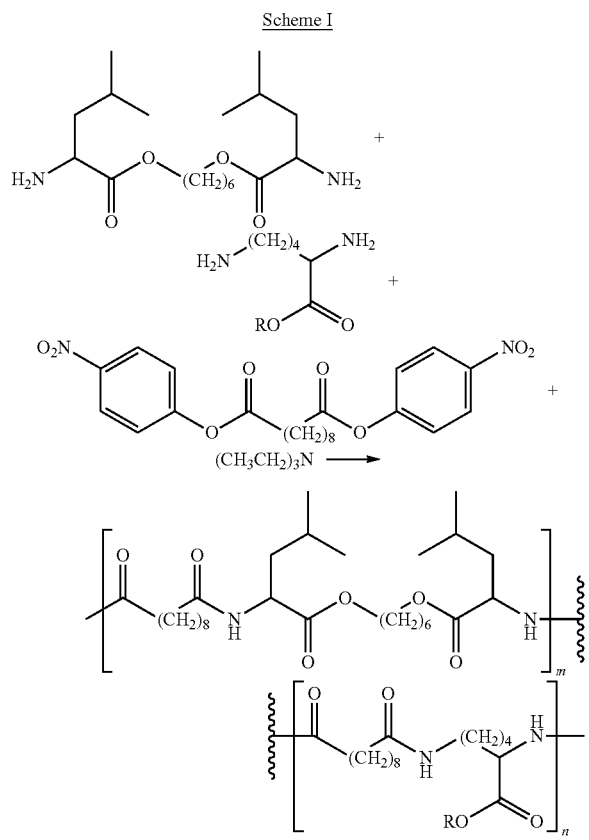

Scheme I

Reactive end groups in PEAs can be problematic. First, since active amino and active carboxyl end groups are present, polymerization can continue. Second, if the PEA formed is combined with a drug that possesses an functional group capable of reacting with a carboxyl (activated or unactivated) or amino group, it is possible that the drug will react and covalently attach to the PEA, essentially rendering the drug unavailable for therapeutic use.

What is needed are PEAs in which the end groups are rendered inactive so as to avoid the above problem and any other than might arise because of the presence of the active terminal functional groups. The present invention provide such PEAs and methods for preparing them.

SUMMARY

Thus, an aspect of the present invention is a poly(ester amide) (PEA) comprising inactivated terminal amino groups and inactivated terminal carboxyl groups wherein the inactivated terminal amino groups are end-capped and the inactivated terminal carboxyl groups are either the free acid, a salt thereof or are end-capped.

In an aspect of this invention, at least 50% of the terminal amino groups have been inactivated and at least 50% of the terminal carboxyl groups have been inactivated.

In an aspect of this invention, at least 90% of the terminal amino groups have been inactivated and at least 90% of the terminal carboxyl groups have been inactivated.

In an aspect of this invention, at least 99% of the terminal amino groups have been inactivated and at least 99% of the terminal carboxyl groups have been inactivated.

In an aspect of this invention, the terminal amino groups or the terminal carboxyl groups are inactivated by reaction with a bioactive agent.

An aspect of this invention is a method of inactivating a poly(ester amide) (PEA), comprising end-capping terminal amino groups by reaction with a first chemical agent and end-capping terminal carboxyl groups with a second chemical agent.

In an aspect of this invention, the first chemical agent or the second chemical agent in the above method is a bioactive agent.

In aspect of this invention is a coating for an implantable medical device comprising the PEA of claim 1.

In an aspect of this invention, the coating further comprising a biocompatible polymer or a biobeneficial or a bioactive agent or any combination thereof.

In an aspect of this invention, in the above coating the implantable medical device is a stent.

In an aspect of this invention, in the above coating, the implantable medical device is a stent.

An aspect of this invention is an implantable medical device formed of a material comprising a PEA of claim 1.

In an aspect of this invention, with regard to the above implantable medical device, the material further comprises a bioactive agent.

In an aspect of this invention with regard to the above coating and the above implantable medical device, the bioactive agent is selected from the group consisting of paclitaxel, docetaxel, estradiol, nitric oxide donors, super oxide dismutases, super oxide dismutase mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propylrapamycin, 40-O-[2-(2-hydroxy)ethoxy]ethylrapamycin, and 40-O-tetrazole-rapamycin, ABT-578, clobetasol, progenitor cell capturing antibody, prohealing drugs, prodrugs thereof, co-drugs thereof, and a combination thereof.

An aspect of this invention is a method of treating or preventing a disorder in a patient in need thereof comprising implanting in the patient an implantable device comprising the coating of claim 12, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

DETAILED DESCRIPTION

As used herein, "poly(ester amide)" or "PEA" refers to a polymer formed by the condensation reaction of a diacid having the general structure

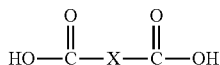

with a diaminodiester having the general structure

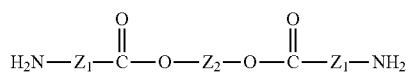

and optionally with a diamine having the general structure $NH_2$—Y—$NH_2$ to afford a compound having the general structure

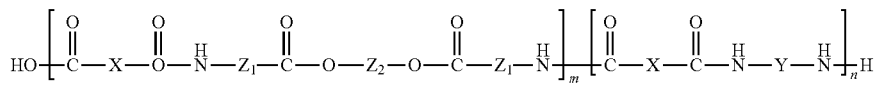

wherein m is an integer, n is 0 or an integer; X, Y, $Z_1$ and $Z_2$ are independently branched or straight chain alkyl, cycloalkyl, alkenyl, alkynyl, aryl, heteroaryl, heteroalicyclic or any combinations thereof and any of which may be optionally substituted. A nonlimiting example of such a PEA is shown in Scheme 1 above. Other exemplary PEAs are described in, e.g., U.S. Pat. No. 6,503,538 B1.

In the synthesis of PEAs it is often desirable to activate the carboxyl groups of the dicarboxy monomer to facilitate the condensation with the diamines. This is most often accomplished by a reaction that substitutes for the hydrogen of the free carboxylic acid (—C(O)OH) or the alkyl group of an inactive ester such as a methyl or ethyl ester (—C(O)OCH$_3$), —C(O)OCH$_2$CH$_3$) an entity that has the property of being a good leaving group. Thus, the carboxyl groups can be activated by any number of methods well-known to those skilled in the art. All such methods as well as any that might be devised in the future are within the scope of this invention. Among these activating functionalities are, without limitation, mononitrophenyl compounds such as p-nitrophenyl, m-nitrophenyl or o-nitrophenyl, dinitrophenyl compounds, trinitrophenyl compounds, and phenyl groups bearing one, two, or three cyano, halogen, keto, ester, or sulfone groups.

The amino groups of the diamine monomer used in the synthesis of the PEA generally need no further activation, they are sufficiently active in their own right.

As used herein, a "terminal amino group" and a "terminal carboxyl group" refer to the groups at the end of PEA chains as exemplified in Scheme I).

As used herein "end-capping" refers to the reaction of a terminal amino group and/or a terminal carboxyl group with one or more moiety(ies) that alters the chemical properties of the terminal group, rendering it less likely to spontaneously react with other functionalized compounds with which they may come in contact such as, in particular for the purposes of this invention, bioactive agents. The thus-altered amino or carboxyl group can be referred to as "inactivated." For the purposes of this invention, "end-capping" a terminal carboxyl group includes simply hydrolyzing or otherwise substituting an activating moiety on the carboxyl group with an hydrogen atom to form the free acid (—C(O)OH) or a salt thereof.

The end-capped PEA may optionally contain in its polymeric matrix one or more biocompatible polymers (that may be biodegradable, bioabsorbable, non-biodegradable, or non-bioabsorbable) other than a PEA, a biobeneficial material, a bioactive agent or any combination of these. As such, the composition can be used to coat an implantable device or to form the implantable device itself, such as, without limitation, a stent.

End-Capping Amino Groups

The amino active groups on the PEA can be end-capped first. The end-capping process is a separate reaction done after the polymerization. The PEA may, or may not be purified before the amino endcapping reaction.

In one embodiment, the active amino group can be end-capped by alkylation of the amino group, forming a quaternary ammonium group:

$$PEA\text{-}NH_2 + RX \rightarrow PEA\text{-}NR_3^+X^-$$

wherein X=Br, Cl, I and R=any primary or secondary alkyl radical having, e.g., 2 to 12 carbon atoms

Scheme II

In another embodiment, the active amino group can be end-capped by reaction with an acid chloride to form an amide:

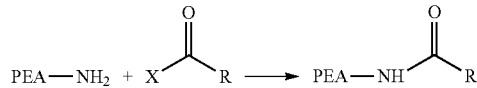

wherein X=Br, Cl, I and R=any primary or secondary alkyl radical having, e.g., 2 to 12 carbon atoms The active amino group can be subjected to reductive amination with an aldehyde in the presence of a reducing agent, e.g., NaCNBH$_3$ and NaBH$_4$:

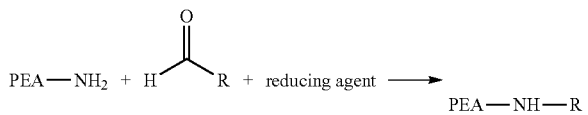

wherein R=any primary or secondary alkyl radical having, e.g., 2 to 12 carbon atoms In still a further embodiment, the active amino group can be rendered inactive by reaction with a diazo compound in the presence of a Lewis acid such as $BF_3$, forming an alkylated amino group:

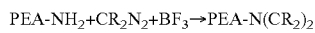
PEA-$NH_2$+$CR_2N_2$+$BF_3$→PEA-N$(CR_2)_2$ wherein R=hydrogen or any primary or secondary alkyl radical having, e.g., 2 to 12 carbon atoms Scheme V In some other embodiments, diazotization of the amine can be used to inactivate an active primary amino group. One example of such diazotization is shown below:

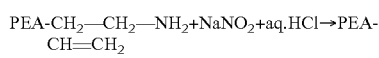
PEA-$CH_2$—$CH_2$—$NH_2$+$NaNO_2$+aq.HCl→PEA-CH=$CH_2$

Scheme VI

Active primary amino groups can be rendered inactive by oxidation, forming a —$NO_2$ group:

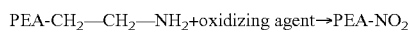
PEA-$CH_2$—$CH_2$—$NH_2$+oxidizing agent→PEA-$NO_2$

Scheme VII

Alternatively, an active amino group on the PEA can react with an anhydride, an epoxide, isocyanate, or isothiocyanate respectively to inactivate the active amino group:

Scheme VIII

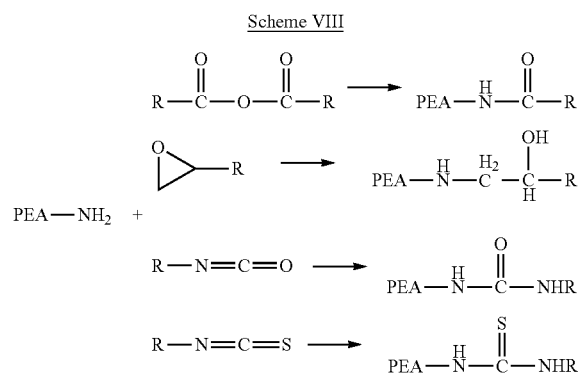

In Scheme VIII, R is an alkyl moiety, which can be saturated or unsaturated, linear or branched alkyl or a cycloalkyl or an aryl moiety. Preferably, R is an alkyl or cycloalkyl with 2-12 carbons.

An active amino group on the PEA may also be inactivated by Michael addition to an α,β-unsaturated ester, ketone, aldehyde or another unsaturated electron-withdrawing group, e.g., —CN:

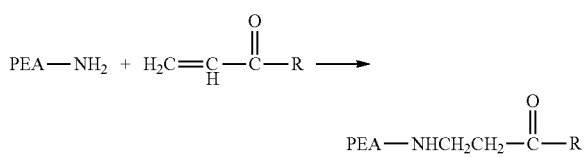

wherein R=hydrogen, any primary or secondary alkyl radical having 2 to 12 carbon atoms, or OR', wherein R'=any primary or secondary alkyl radical having, e.g., 2 to 12 carbon atoms End-Capping Carboxyl Groups The carboxyl groups or activated carboxyl groups on the PEA can be inactivated by reaction with a primary amine, a secondary amine, heterocyclic amine, a thiol, alcohol, malonate anion, carbanion, or other nucleophilic group. For example, PEA with a p-nitrophenyl carboxyl end group can be inactivated as follows:

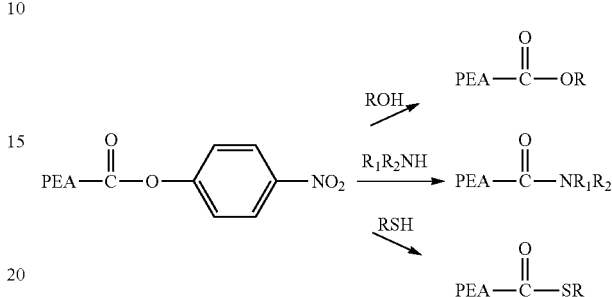

wherein R=any carbon alkyl, or unsaturated, linear or branched, with, e.g. 2 to 12 carbon atoms; $R_1$, $R_2$=H or any alkyl radical having, e.g., 2 to 12 carbon atoms or $R_1$, $R_2$ may also be alkyl ether, alkyl hydroxyl such as 2-hydroxyethyl Alternatively, the p-nitrophenyl carboxyl group on the PEA can be hydrolyzed under acidic or basic conditions so as to form a free carboxylic acid group or carboxylate group (Scheme XI):

Scheme XI

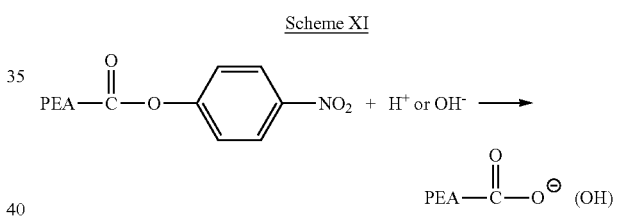

Or the p-nitrophenol ester may also be reacted with reducing agents such as sodium borohydride or sodium cyanoborohydride to convert the ester to a hydroxyl group.

Other means of inactivating the carboxyl group will become apparent to those skilled in the art based on the disclosures herein. All such inactivating techniques are within the scope of this invention.

Biocompatible Polymer

The biocompatible polymer that can be used with the end-capped PEA in the coatings or medical devices described herein can be any biocompatible polymer known in the art, which can be biodegradable or nondegradable. Representative examples of polymers that can be used to coat an implantable device in accordance with the present invention include, but are not limited to, ethylene vinyl alcohol copolymer (EVOH, EVAL), poly(hydroxyvalerate), poly(L-lactic acid), poly(L-lactide), poly(D,L-lactide), poly(L-lactide-co-D,L-lactide), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(D,L-lactide-co-glycolide) (PDLLAGA), poly(glycolic acid-co-trimethylene carbonate), polyphosphoester, polyphosphoester urethane, poly(amino acids), polycyanoacrylates, poly(trimethylene carbonate), poly(iminocarbonate), poly(butylene terephthalate-co-PEG-terephthalate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as vinylidene fluoride (without limitation Solef™ or Kynar™), polyvinylidene fluoride (PVDF) or poly(vinylidene-co-hexafluoropropylene) (PVDF-co-HFP), polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

The biocompatible polymer can provide controlled release of a bioactive agent if such is included in the coating and/or if binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,581,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. Additional ways to control the release of the bioactive agent are specifically designing the polymer coating construct, conjugating the active agent onto the polymeric backbone, designing a micro-phase-separated PEA where the agent resides in the more mobile segment, and designing a PEA in which the bioactive has an appropriate level of solubility. One of ordinary skill in the art can readily select a carrier system using a biocompatible polymer to provide a controlled release of the bioactive agent. Examples of the controlled release carrier system can come from the examples provided above; however, other possibilities not provided are also achievable.

A presently preferred biocompatible polymer is a polyester, such as PLA, PLGA, PGA, PHA, poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), and a combination thereof, and polycaprolactone (PCL).

Bioactive Agents

The end-capped PEA described herein can form a coating on an implantable medical device or can form the device itself where one or more bioactive agents are contained in the polymeric matrix. The bioactive agent(s) can be any which has a therapeutic, prophylactic or diagnostic effect. These agents can have, without limitation, anti-proliferative, anti-inflammmatory, antineoplastic, antiplatelet, anti-coagulant, anti-fibrin, antithrombonic, antimitotic, antibiotic, antiallergic, antioxidant or cystostatic properties. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin, 40-O-(2-hydroxy)ethyl-rapamycin (everolimus), methyl rapamycin (ABT-578), 40-O-(3-hydroxy)propyl-rapamycin, 40-O-[2-(2-hydroxy)ethoxy]ethyl-rapamycin, 40-O-tetrazole-rapamycin, paclitaxel and, docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of antiplatelet, anticoagulant, antifibrin and antithrombin compounds include, again without limitation, sodium heparin, low molecular weight heparins, heparinoids, hirudin, argatroban, forskolin, vapiprost, prostacyclin, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl(4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the tissues being delivered to; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Biobeneficial Material

The biobeneficial material that can be used with the endcapped PEA to form a coating on or an implantable medical device per se as described herein can be a polymeric material or non-polymeric material. The biobeneficial material is preferably flexible, biocompatible and biodegradable. A biobeneficial material is one which enhances the biocompatibility of a device by being non-fouling, hemocompatible, actively non-thrombogenic, or anti-inflammatory, all without depending on the release of a pharmaceutically active agent.

Generally, a biobeneficial material has a relatively low glass transition temperature ($T_g$). In some embodiments, the $T_g$ is below human body temperature. This attribute renders the biobeneficial material relatively soft as compared to the biocompatible polymer and allows a layer of coating containing the biobeneficial material to fill any surface damages that may arise when an implantable medical device is coated with a layer comprising the biocompatible polymer. For example, during radial expansion of the stent, a more rigid biocompatible polymer can crack or have surface fractures. A softer biobeneficial material can fill in the crack and fractures.

Another attribute of a biobeneficial material is hydrophilicity. The hydrophilicity of the biobeneficial agent contributes to the overall hydrophilicity of the coating containing the agent. Generally, the higher the hydrophilicity of a coating, the higher the drug release rate from that coating and the higher the degradation rate of the coating.

Representative biobeneficial materials include, but are not limited to, polyethers such as poly(ethylene glycol), copoly (ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof.

In a preferred embodiment, the biobeneficial material is a block copolymer having flexible poly(ethylene glycol) and poly(butylene terephthalate) blocks (PEG/PBT, e.g., PolyActive™). PolyActive™ includes AB, ABA and BAB copolymers where A is PEG and B is PBT.

Examples of Implantable Medical Devices

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316 L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable medical device or prosthesis, e.g., a stent. For coatings including one or more active agents, the agent will be retained on the device during delivery and expansion and then will be released at a desired rate and for a predetermined duration at the site of implantation. Preferably at present, the medical device is a stent. A stent having the above-described coating is useful for a variety of medical procedures, including, without limitation, treatment of obstructions caused by tumors in bile ducts, esophagus, trachea/bronchi and other biological passageways. A stent having the above-described coating is particularly useful for treating occluded regions of blood vessels caused by atherosclerosis, abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

EXAMPLES

The following examples are for illustrative purposes only and are not intended nor should they be construed as limiting the scope of this invention in any manner.

Example 1

Preparation of co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of di-p-toluenesulfonic acid salt of bis-(L-leucine)-1,6-hexylene diester (120.4 g, 0.18 mole), di-p-toluenesulfonic acid salt of L-lysine benzyl ester (11.61 g, 0.02 mole), and di-p-nitrophenyl sebacinate (88.88 g, 0.2 mole) in dry DMF (110 ml). The mixture is stirred and heated at 80° C. for 12 hours.

Example 2

The active amino end groups on the PEA prepared in Example 1 can be endcapped as follows: While stirring, the DMF/PEA solution of Example 1 is cooled to 0° C. Triethylamine (0.0057 mole) is added and acetyl chloride (0.448 g, 0.0057 mole) is added dropwise to the mixture. Stirring is continued for 12 hours while the solution is allowed to equilibrate to room temperature. The solution is diluted with ethanol (300 ml), and poured into one liter of deionized water. The precipitated polymer is collected, extracted with two, one liter portions of phosphate buffer (0.1M, pH 7), a final, one liter portion of deionized water, isolated by suction filtration, and vacuum dried at 40° C.

Example 3

The active amino endgroups on the PEA prepared in Example 1 can also be endcapped as follows: Ethyl acrylate (0.571 g, 0.0057 mole) is added to the DMF/PEA solution of Example 1. Phosphoric acid (0.011 g, 0.000114 mole) is added as an acid catalyst. With stirring, the solution is heated to 100° C. and stirred for 60 minutes. The solution is diluted with ethanol (300 ml), and poured into one liter of deionized water. The precipitated polymer is collected, extracted with two, one liter portions of phosphate buffer (0.1M, pH 7), a final, one liter portion of deionized water, isolated by suction filtration, and vacuum dried at 40° C.

Example 4

A medical article with two layers can be fabricated to comprise everolimus by preparing a first composition and a second composition, wherein the first composition is a layer containing a bioactive agent which includes a matrix of the PEA of Example 2 and a bioactive agent, and the second composition is a topcoat layer comprising the PEA of Example 2. The first composition can be prepared by mixing about 2% (w/w) of the PEA of Example 2 and about 0.33% (w/w) everolimus in absolute ethanol, sprayed onto a surface of a bare, 12 mm VISION™ stent (Guidant Corp.) and dried to form a coating. An exemplary coating technique involves spray coating with a 0.014 fan nozzle, a feed pressure of about 0.2 atm, and an atomization pressure of about 1.3 atm; applying about 20 µg of wet coating per pass; drying the coating at about 62° C. for about 10 seconds between passes and baking the coating at about 50° C. for about 1 hour after the final pass to form a dry agent layer. The layer containing a bioactive agent would be comprised of about 336 µg of the PEA of Example 2 and about 56 µg of everolimus. The second composition can be prepared by mixing about 2% (w/w) of the PEA of Example 2 in absolute ethanol. The solution is then applied over the dried agent layer using the same coating technique above. The topcoat would contain about 400 µg of the PEA of Example 2. The total weight of the stent coating would be about 792 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A polymer of formula:

PEA-Inactivated Terminal Amino Group or

Inactivated Terminal Carboxyl Group-PEA;

wherein PEA comprises formula I:

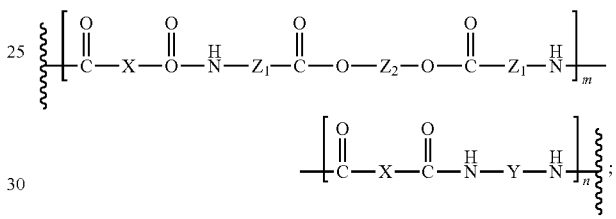

wherein:

m is an integer;

n is 0 or an integer;

$X, Y, Z_1$ and $Z_2$ are each independently branched or straight chain alkylene, cycloalkylene, alkenylene, alkynylene, arylene, heteroarylene, or heterocycloalkylene;

Inactivated Terminal Carboxyl Group is: $-C(O)NR_1R_2$, wherein $R_1$ and $R_2$ are H, 2 to 12 carbon alkyl, alkyl ether, or alkyl hydroxyl; or $-C(O)SR$, wherein R is 2 to 12 carbon alkyl; and Inactivated Terminal Amino Group is: $-NR_3+X^-$, wherein X is Br, Cl, or I, and each R is a primary or secondary alkyl radical having 2 to 12 carbon atoms; $-NHC(O)R$, wherein R is a primary or secondary alkyl radical having 2 to 12 carbon atoms; $-NHR$, wherein R is a primary or secondary alkyl radical having 2 to 12 carbon atoms; $-N(C(R)_3)_2$, wherein each R is hydrogen or a primary or secondary alkyl radical having 2 to 12 carbon atoms; $-CH=CH_2$; $-NO_2$; $-NHC(O)R$, wherein R is cycloalkyl, aryl, or a saturated, linear or branched alkyl; $-NHCH_2CH(OH)R$, wherein R is cycloalkyl, aryl, or a saturated, linear or branched alkyl; $-NHC(O)NHR$, wherein R is cycloalkyl, aryl, or a saturated, linear or branched alkyl; $-NHC(S)NHR$, wherein R is cycloalkyl, aryl, or a saturated, linear or branched alkyl; or $-NHCH_2CH_2C(O)R$, wherein R is hydrogen, a primary or secondary alkyl radical having 2 to 12 carbon atoms, or OR', wherein R' is a primary or secondary alkyl radical having 2 to 12 carbon atoms.

2. A coating for an implantable medical device comprising the polymer of claim 1.

3. The coating of claim 2, wherein the implantable medical device is a stent.

* * * * *